(12) United States Patent
Spiegl et al.

(10) Patent No.: US 12,730,103 B2
(45) Date of Patent: Sep. 8, 2026

(54) FORMWORK PANEL FOR A FORMWORK STRUCTURE

(71) Applicant: PERI SE, Weissenhorn (DE)

(72) Inventors: Andreas Spiegl, Weissenhorn (DE); Guenther Staudenrausch, Weissenhorn (DE)

(73) Assignee: PERI SE, Weissenhorn (DE)

( * ) Notice: Subject to any disclaimer, the term of this patent is extended or adjusted under 35 U.S.C. 154(b) by 295 days.

(21) Appl. No.: 17/787,172

(22) PCT Filed: Dec. 15, 2020

(86) PCT No.: PCT/EP2020/086213
§ 371 (c)(1),
(2) Date: Jun. 17, 2022

(87) PCT Pub. No.: WO2021/122592
PCT Pub. Date: Jun. 24, 2021

(65) Prior Publication Data

US 2023/0023964 A1 Jan. 26, 2023

(30) Foreign Application Priority Data

Dec. 17, 2019 (DE) .................... 10 2019 219 918.6

(51) Int. Cl.
*G01N 33/38* (2006.01)
*E04G 9/10* (2006.01)

(52) U.S. Cl.
CPC ............ *G01N 33/383* (2013.01); *E04G 9/10* (2013.01)

(58) Field of Classification Search
CPC .... G01N 33/383; E04G 9/10; B28B 17/0081; B28B 7/0002
USPC ........................................................ 702/189
See application file for complete search history.

(56) References Cited

U.S. PATENT DOCUMENTS

| | | | | |
|---|---|---|---|---|
| 4,900,920 | A * | 2/1990 | Federmann | G01L 1/242 250/227.17 |
| 7,875,870 | B2 * | 1/2011 | Maruyama | G11B 17/0408 250/559.4 |
| 8,663,779 | B2 | 3/2014 | Koegl | |
| 2005/0268699 | A1 * | 12/2005 | Papakostas | G01L 1/20 73/46 |
| 2007/0046479 | A1 | 3/2007 | Hines | |
| 2011/0062950 | A1 * | 3/2011 | Feledziak | G01D 3/032 324/207.25 |
| 2014/0239147 | A1 | 8/2014 | Hayasaki | |

(Continued)

FOREIGN PATENT DOCUMENTS

| | | |
|---|---|---|
| CN | 107989634 | 5/2018 |
| CN | 109425729 | 3/2019 |

(Continued)

OTHER PUBLICATIONS

Yoshiyuki, KR 20110006032 A, " Blood flow measuring machine and brain activity measuring machine using blood flow measuring machine", Date published: Jan. 20, 2011 (Year: 2011).*

(Continued)

*Primary Examiner* — John H Le
(74) *Attorney, Agent, or Firm* — Jones Day

(57) ABSTRACT

A formwork panel for a formwork device for creating wall or ceiling sections in fresh concrete construction with a sensor integrated in the formwork panel.

21 Claims, 2 Drawing Sheets

(56) References Cited

U.S. PATENT DOCUMENTS

| | | | | |
|---|---|---|---|---|
| 2015/0069647 | A1 | 3/2015 | Ciuperca | |
| 2015/0069664 | A1 | 3/2015 | Ciuperca | |
| 2017/0254202 | A1* | 9/2017 | Kern | E21D 11/10 |
| 2018/0009712 | A1 | 1/2018 | Ciuperca | |
| 2018/0045621 | A1 | 2/2018 | Radjy | |
| 2018/0216354 | A1* | 8/2018 | Bartel-Lingg | E04F 15/12 |
| 2019/0324012 | A1 | 10/2019 | Radjy | |

FOREIGN PATENT DOCUMENTS

| | | |
|---|---|---|
| CN | 110259110 | 9/2019 |
| DE | 102008007015 | 8/2008 |
| DE | 102008000381 | 8/2009 |
| DE | 102010036758 | 2/2012 |
| EP | 2743427 | 6/2014 |
| EP | 3216979 | 9/2017 |
| JP | 2019178868 | 10/2019 |
| WO | 2007025172 | 3/2007 |
| WO | 2013021951 | 2/2013 |

OTHER PUBLICATIONS

Zhao et al, CN 105547638 B, “A Thin Layer Water Flow Rolling-measuring System and Method Based on Pressure Sensor”, Date published: 03/127/2018 (Year: 2018).*

Hao et al., CN 105241770 A, “A Magnetic Induction Type Return Sensor”, Date published: Jan. 13, 2016 (Year: 2016).*

Feng et al. , CN 109269694 A, “Flexible Tactile Sensing Device, System and Manufacturing Method Thereof”, Date published: Jan. 25, 2019 (Year: 2019).*

* cited by examiner

FORMWORK PANEL FOR A FORMWORK STRUCTURE

REFERENCE TO RELATED APPLICATIONS

This application claims priority to German Patent Application No. 10 2019 219 918.6, filed Dec. 17, 2019, which is incorporated herein by reference in its entirety.

FIELD OF INVENTION

The present invention relates to a formwork panel for a formwork device (formwork structure) for producing wall or ceiling sections in fresh concrete construction, a formwork device with a corresponding formwork panel, the use of a sensor for integration in a formwork panel of a formwork device, a computing unit for a formwork panel of a formwork device, a program element, a computer-readable medium, and a method for determining a point in time at which the poured concrete is sufficiently solidified to produce a further, overlying wall section and/or at which the formwork panel can be removed from the formwork at the earliest.

BACKGROUND

In concrete construction, wall or ceiling sections are created by means of a formwork device, which comprises formwork panels that form a cavity into which the concrete can be poured.

Particularly in the construction of multi-storey concrete buildings, these wall or floor slab sections are produced sequentially, section by section. Once the concrete in the corresponding section is sufficiently consolidated, the formwork panels can be removed and another wall section or floor slab section can be produced above it.

SUMMARY

It is an object of the present invention to increase efficiency in the construction of wall or floor slab sections in fresh concrete construction.

This object is solved by the features of the independent patent claims. Further embodiments of the invention result from the subclaims and the following description of embodiments.

A first aspect of the present disclosure relates to a formwork panel for a formwork device for producing wall or ceiling sections in fresh concrete construction. The formwork panel has a concrete-contacting layer which is arranged to come into direct contact with the concrete to be filled into the formwork device. A sensor is also provided, which is integrated into the formwork panel.

The term "sensor" is to be interpreted broadly. The sensor may be a single sensor, for example in the form of a plate or foil, which is arranged in or close to the layer in contact with the concrete within the formwork panel. In particular, however, it may also be a sensor arrangement comprising several interconnected or separate sensors.

The formwork device usually has several formwork panels and one or more corresponding frames that fix the formwork panels.

The layer of the formwork panel in contact with the concrete can also be referred to as the formwork skin. In particular, it can take the form of a coating, for example of phenolic resin or a comparable material, in order to form as smooth and even a surface as possible. This is particularly advantageous for exposed concrete construction.

According to an embodiment, the sensor is configured to record measurement data from which a point in time can be calculated at which the filled concrete is sufficiently consolidated to produce a further, overlying wall section. It can be provided that for the calculation of this point in time additional information is used, which is not recorded by the sensor itself. This can be, for example, information about the formwork panel or the formwork device, the outside temperature, usage data of the formwork panel, such as the frequency of its use, or also data obtained by fatigue measurements, such as an elongation load on the formwork panel, a pressure load on the formwork panel, and in particular extreme events that can shorten the service life of the formwork panel, such as overpressure loads or extreme temperatures.

According to an embodiment, the sensor is configured to record measurement data from which a time can be calculated at which the formwork panel can be removed at the earliest in order to form the concrete. For this purpose, the concrete must be sufficiently consolidated.

According to an embodiment, the sensor is configured measure a temperature, a pressure, a humidity, a tensile force, an elongation, a bending and/or a pH value. The more different data are recorded, the more precisely the time can be determined at which the formwork panel can be removed at the earliest and/or at which a further, overlying wall section can be created.

According to another embodiment, the sensor has a self-sufficient internal power supply, for example in the form of one or more batteries or other energy storage devices, such as a capacitor.

It can be provided that the energy storage of the sensor can be charged via an energy supply interface when, for example, the formwork panel is stored for further use. In particular, a wireless energy supply interface could be provided for this purpose, which is designed inductively, for example. However, it is also possible for the energy supply interface to be wired, for example in the form of interface connections that are accessible on the rear side of the formwork panel, i.e. on the side facing away from the concrete, or on the side surface of the formwork panel.

According to a further embodiment, the sensor is arranged directly behind the layer in contact with the concrete. For example, it touches the layer in contact with the concrete on its rear side.

According to another embodiment, the formwork panel comprises a panel core, which may also be referred to as a core panel, wherein the sensor is arranged between the layer in contact with the concrete and the panel core or within the panel core.

According to a further embodiment, the sensor is arranged inside the layer in contact with the concrete, for example in a recess on the back of the layer in contact with the concrete, i.e. on the side facing away from the concrete.

According to a further embodiment, the sensor has a wireless communication interface that is set up to transmit the measurement data collected by the sensor to an external computing unit. The external computing unit can be a server, for example, which collects and evaluates the data from a large number of sensors.

Another aspect of the present disclosure relates to a formwork device or formwork structure comprising a formwork panel described above and below.

Another aspect of the present disclosure relates to the use of a sensor for integration into a formwork panel of a formwork device.

Another aspect of the present disclosure relates to a computing unit for a formwork panel of a formwork device, the computing unit being arranged to receive measurement data from a sensor of the formwork panel, and to calculate therefrom a time at which the poured concrete is sufficiently consolidated to produce a further, overlying wall section, and/or at which the formwork panel can be removed at the earliest.

Another aspect of the present disclosure relates to a program element which, when executed on a computing unit for a formwork panel of a formwork apparatus, instructs the computing unit to receive measurement data from a sensor of the formwork panel to calculate therefrom a time at which the poured concrete is sufficiently consolidated to produce a further overlying wall section and/or at which the formwork panel can be removed at the earliest.

The program element may, for example, be loaded and/or stored in a main memory of a data processing device, such as a data processor of a computing unit, wherein the data processing device may also be part of an embodiment of the present invention. This data processing device may be arranged to perform method steps of the method described above. The data processing device may further be arranged to execute the computer program and/or the method automatically and/or to execute input from a user. The computer program may also be provided over a data network, such as the Internet, and downloaded from such a data network into the memory of the data processing device. The computer program may also comprise an update to an existing computer program, whereby the existing computer program may be enabled to perform the method described above, for example.

Another aspect of the present disclosure relates to a computer-readable medium on which a program element described above is stored.

The computer-readable medium may be, in particular, but not necessarily, a non-volatile medium that is particularly suitable for storing and/or distributing a computer program. The computer-readable storage medium may be a CD-ROM, a DVD-ROM, an optical storage medium, a solid-state medium, or the like, provided with or as part of other hardware. Additionally or alternatively, the computer-readable storage medium may be distributed or distributed in other forms, such as over a data network, such as the Internet or other wired or wireless telecommunications systems. For this purpose, the computer-readable storage medium may take the form of one or more data packets, for example.

Another aspect of the present disclosure relates to a method for determining a point in time of a formwork panel of a formwork device at which the filled concrete is sufficiently consolidated to produce a further, overlying wall section and/or at which the formwork panel can be removed at the earliest. In the method, measurement data is acquired by a sensor of the formwork panel, followed by a calculation of a point in time on the basis of the measurement data and, if necessary, further information, at which the filled-in concrete is sufficiently consolidated to produce a further, overlying wall section and/or at which the formwork panel can be removed at the earliest.

Further embodiments are described below with reference to the figures. If the same reference signs are used in the following description of figures, these designate the same or similar elements. The illustrations in the figures are schematic and not to scale.

DETAILED DESCRIPTION OF EMBODIMENTS

Figure 1:
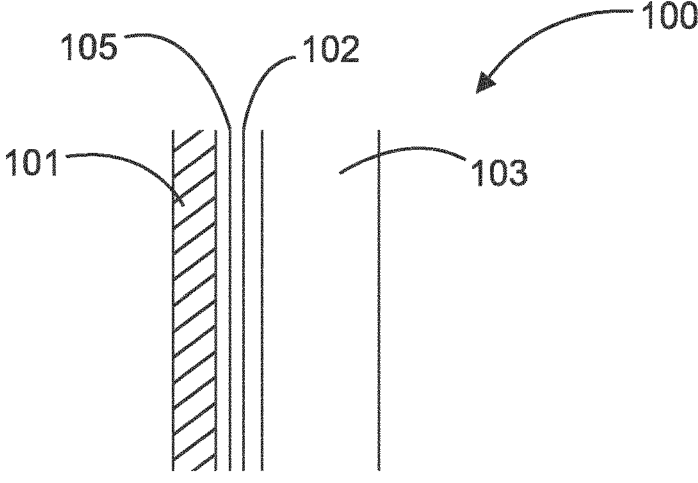
FIG. 1 shows a cross-sectional view of a formwork panel according to an embodiment.
Figure 6:
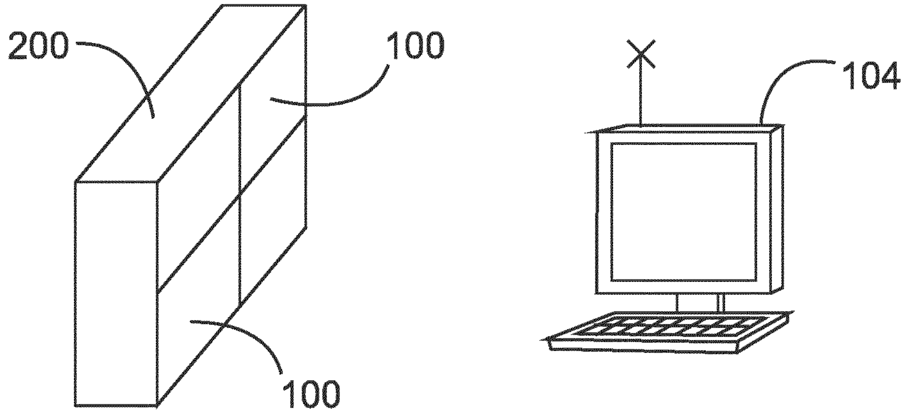
FIG. 6 shows a formwork device and a computing unit according to an embodiment.

FIG. 1 shows a cross-sectional view of a formwork panel 100 for a formwork device 200 (cf. FIG. 6). The formwork panel 100 has a concrete-contacting layer 101, for example in the form of a phenolic resin coating. The concrete-contacting layer 101 is arranged to come into direct contact on its outer side (the left side in the figure) with the concrete to be poured into the formwork device. A sensor 102 is provided, which may be flat or plate-like, for example in the form of one or more sensor plates. The sensor may have a circular cross-section, which may facilitate subsequent integration of the sensor into the formwork panel.

A nonwoven fabric 105 may be disposed between the "sensor layer" in which the sensor 102 is located and the concrete-contacting layer 101. On the other side of the sensor layer is a plate core 103, which may also be referred to as a core or core plate. This plate core may be made of veneer wood or may be made of plastic.

Thus, in the embodiment of FIG. 1, the sensor is located behind the nonwoven 105.

Figure 2:
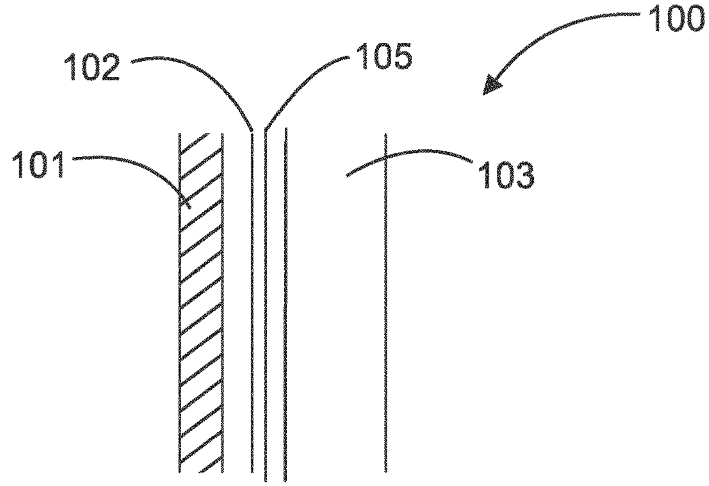
FIG. 2 shows a cross-sectional view of a formwork panel according to a further embodiment.

FIG. 2 shows a cross-sectional view of a formwork panel 100 according to a further embodiment, in which the sensor 102 is located in front of the nonwoven 105, i.e. between the nonwoven 105 and the layer in contact with the concrete (wear layer) 101.

Figure 3:
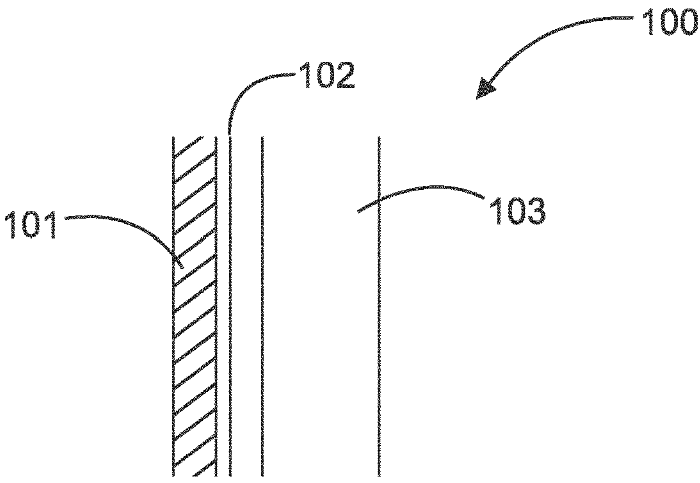
FIG. 3 shows a cross-sectional view of a formwork panel according to a further embodiment.

In the embodiment shown in FIG. 3, no fleece is provided. The plane in which the sensor 102 is located is arranged directly behind the layer 101 in contact with the concrete.

Figure 4:
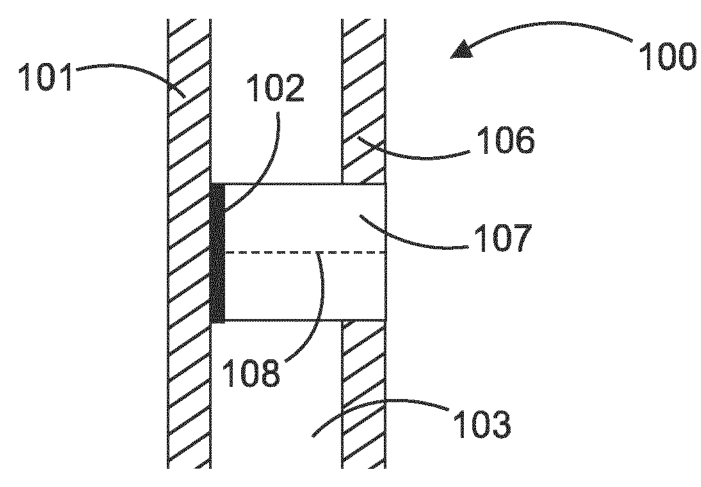
FIG. 4 shows a cross-sectional view of a formwork panel according to a further embodiment.

FIG. 4 shows another embodiment of the formwork panel 100 in which the sensor 102 is arranged directly under the layer 101 in contact with the concrete. This is a retrofit solution in which the sensor is installed in the formwork panel 100 from behind (i.e. from the right-hand side). This can be done by means of a cylindrical hole or recess which extends to the rear side of the layer 101 in contact with the concrete, so that the sensor, which is subsequently inserted into the recess, contacts the layer in contact with the concrete from behind.

The sensor includes a sensor cable 108, which may be used to charge the sensor and/or provide a communication link, and which protrudes from the rear of the formwork panel 100 or is flush with the surface of the formwork panel. A cover plug 107 may be provided, which is press-fitted into the recess, and is sealingly applied to the edge of the recess so that liquid cannot enter the panel.

Figure 5:
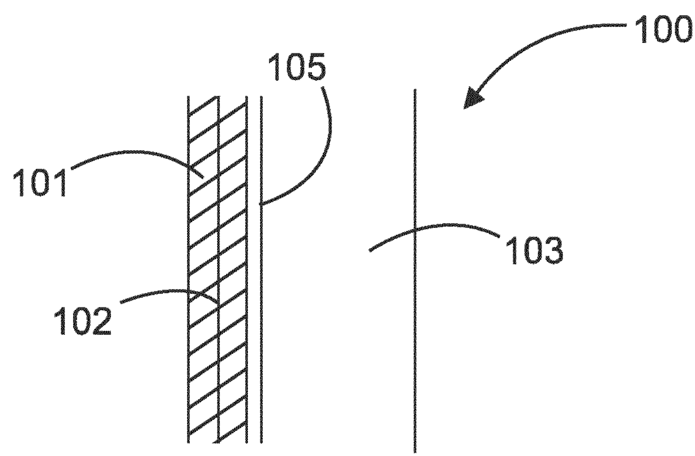
FIG. 5 shows a cross-sectional view of a formwork panel according to a further embodiment.

In the embodiment shown in FIG. 5, the sensing plane is located within the layer 101 in contact with the concrete. In particular, the sensor 102 can be cast into the layer in contact with the concrete during production of the formwork panel.

FIG. 6 shows a formwork device 200, which has several formwork panels 100 and a support frame. The liquid concrete can be poured in from above.

A computing unit 104 is provided that can wirelessly receive measurement data from the sensors integrated into the formwork panels, and then evaluate the data to calculate the appropriate time to form and/or create another wall section.

The sensor 102 may be in the form of a platelet, can, layer, conductive wire, disc, box, or fluid or media filled chamber, or a combination thereof. When the sensor 102 is installed, the formwork panel 100 can be provided with a recess, a cutout, a depression in the wood or panel body from the side facing away from the concrete surface, which serves as a receptacle for the sensor. The recess is adapted to the shape and design of the sensor. The recess is produced by milling, drilling, compacting, embossing or the like. To enable the sensor to transmit data, it is glued, cast (e.g. epoxy resin), inserted, molded, melted, woven, sewn, printed or injected into the recess.

Also, the sensor 102 may be embedded between the concrete-contacting layer 101 and the plate core 103. For example, the layer 101 in contact with the concrete has two or more layers and the sensor 102 is inserted or embedded between these layers.

It is also possible that an additional sensor layer is inserted. The core of the formwork panel can also be covered with a "multilayer" layer. The sensor technology is embedded in this layer. One or more of the layers can be formed as a nonwoven layer. The non-woven layer is, for example, part of the "wear layer", which is also referred to as the concrete-contacting layer, if this is formed from a material, for example polypropylene, which can only be bonded to the core of the panel under certain measures. In this case, the nonwoven layer mediates the connection between the wear layer and the core of the panel and can simultaneously contain the embedded sensor technology, which is inserted, molded in, fused in, glued in, woven in, sewn in, printed or injected.

The sensor can be read and/or supplied with energy via connections or interfaces. The sensor can have its own, for example rechargeable, energy storage or be passive.

Wireless readout of the sensor may also be provided, for example using short-range communication technology such as Bluetooth, NFC, or GSM.

The measured values can be stored in a cloud, passed on to a display element, stored for further use, for example for so-called Building Information Modeling (BIM).

The measured values can also be made available to an artificial intelligence, which evaluates and processes them in software-technical evaluation and calculation systems.

In addition, the sensor can also be set up to record, store and pass on data on position, ambient conditions, duration of use, etc.

The sensor embedded in the formwork panel can be used to directly record the duration of use and conditions of use of the formwork panel, in particular a cycle or concreting cycle counter can be provided. Recommendations for formlining replacement or repair can be derived from this. At the same time, data on the use of the formwork panel can be recorded.

This allows the optimum time for maintenance or replacement of the formwork panel to be calculated.

Depending on the sensor system selected, information on the condition of the formlining surface can be derived. From this, recommendations can be calculated for the use of the formwork sheet (for example, for fair-faced concrete), but also for the possible remaining service life, number of cycles of the formwork sheet etc. The collected data about the formwork sheet can be stored, for example by means of RFID, and used for logistics or billing/maintenance purposes.

In particular, a combined sensor/data storage/output/recording system can be provided. The recorded values can be used as a basis for a usage-dependent calculation of the rental price of the formwork panel. Also, the data can be used to control maintenance. Demand analyses can also be carried out on the basis of the recorded data, and the data can be used for order optimization in maintenance/refurbishment.

The sensor can be designed as an ultrasonic sensor, for example. The reflection wave pattern can provide information about the condition of the formwork surface (wear, cleaning condition, concrete adhesion). Ultrasonic cleaning of the formwork surface, for example by the sensor, can also be provided.

The sensor can be designed as a retrofit solution so that existing formwork panels can be easily retrofitted with the sensor. For this purpose, a recess is made, for example milled, in the back, i.e. the side of the formwork panel facing away from the concrete, and the sensor provided as a finished unit is inserted. This can be done in a similar way to repairing with wood, plastic or metal plates. The sensor can be located close to the wear layer (layer in contact with the concrete).

The wear layer can be adapted for use with the sensor system, for example heat-conducting or pressure-conducting. The aim is to achieve rapid transmission of the concrete conditions (in particular temperature, pressure, etc.) to the sensor. For temperature transmission, the material of the layer in contact with the concrete can be provided with conductive admixtures or consist of a conductive material.

The arrangement of the sensors in the surface of the layer in contact with the concrete or in another layer can be net-like, band-like, flat, point-like, linear, circular, rectangular or elliptical. The number and arrangement of the sensors can be selected in such a way that a reliable statement about the situation in the layer in contact with the concrete is possible, i.e. statistically reliable, and a practical, usable measurement result is generated.

In particular, this allows cycle times to be reduced thanks to more accurate, faster and more consistent measured values. There is no influence on the cleaning process of the formlining and the formwork element, and there is no influence on the construction process. In particular, the concrete quality can be improved. Also, there is no injury to the surface of the layer in contact with the concrete. The measurement result is preferably recorded as close as possible to the concrete surface. Transit losses can thus be reduced. The sensors can, for example, be retrofitted independently of the system and quickly replaced, are BIM-capable and enable statements to be made about the condition, use, location, users and/or service life of the formwork panel.

It is possible to determine or predict the appropriate time for a slab replacement by detecting the degree of contamination. Advantageously, no foreign objects such as sensors need to be inserted into the concrete for this purpose. The sensors are reusable because they are integrated in the formwork panel and do not remain in the concrete. The layer in contact with the concrete is not damaged by the attachment of the sensor, in particular it is not drilled through, milled through or penetrated.

Supplementally, it should be noted that "comprising" and "having" do not exclude other elements or steps, and the indefinite articles "a" or "an" do not exclude a plurality. It should further be noted that features or steps that have been described with reference to any of the above embodiments may also be used in combination with other features or steps of other embodiments described above. Reference signs in the claims are not to be regarded as limitations.

The invention claimed is:

1. A formwork panel for a formwork device for producing wall or ceiling sections in fresh concrete construction, comprising:
- a concrete-contacting layer configured to come into direct contact with the concrete to be poured into the formwork device;
- a plurality of sensors integrated in the formwork panel;
- wherein the plurality of sensors are arranged on the rear side of the concrete-contacting layer, such that the plurality of sensors touches the rear side of the concrete-contacting layer, wherein an arrangement of the plurality of sensors is net.

2. The formwork panel according to claim 1,
- wherein the plurality of sensors are configured to measure one or more of a temperature, a pressure, a humidity, a tensile force, an elongation, a bending, or a PH value.

3. The formwork panel according to claim 1,
- where the plurality of sensors have a self-sufficient power supply.

4. The formwork panel according to claim 1,
- wherein the formwork panel comprises a panel core,
- wherein the plurality of sensors are disposed between the concrete-contacting layer and the panel core or within the panel core.

5. The formwork panel according to claim 1,
- wherein the plurality of sensors comprise a wireless communication interface configured to transmit the measurement data to an external computing unit, and/or
- wherein the plurality of sensors include a power supply interface configured to charge an energy storage device of the sensor.

6. A formwork device comprising the formwork panel according to claim 1.

7. A formwork panel for a formwork device for producing wall or ceiling sections in fresh concrete construction, comprising:
- a concrete-contacting layer configured to come into direct contact with the concrete to be poured into the formwork device;
- a plurality of sensors integrated in the formwork panel;
- wherein the plurality of sensors are arranged on the rear side of the concrete-contacting layer, such that the plurality of sensors touches the rear side of the concrete-contacting layer, wherein an arrangement of the plurality of sensors is flat.

8. The formwork panel according to claim 7,
- wherein the plurality of sensors are configured to measure one or more of a temperature, a pressure, a humidity, a tensile force, an elongation, a bending, or a PH value.

9. The formwork panel according to claim 7,
- wherein the formwork panel comprises a panel core,
- wherein the plurality of sensors are disposed between the concrete-contacting layer and the panel core or within the panel core.

10. A formwork panel for a formwork device for producing wall or ceiling sections in fresh concrete construction, comprising:
- a concrete-contacting layer configured to come into direct contact with the concrete to be poured into the formwork device;
- a plurality of sensors integrated in the formwork panel;
- wherein the plurality of sensors are arranged on the rear side of the concrete-contacting layer, such that the plurality of sensors touches the rear side of the concrete-contacting layer, wherein an arrangement of the plurality of sensors is linear.

11. The formwork panel according to claim 10,
- wherein the plurality of sensors are configured to measure one or more of a temperature, a pressure, a humidity, a tensile force, an elongation, a bending, or a PH value.

12. The formwork panel according to claim 10,
- wherein the formwork panel comprises a panel core,
- wherein the plurality of sensors are disposed between the concrete-contacting layer and the panel core or within the panel core.

13. A formwork panel for a formwork device for producing wall or ceiling sections in fresh concrete construction, comprising:
- a concrete-contacting layer configured to come into direct contact with the concrete to be poured into the formwork device;
- a plurality of sensors integrated in the formwork panel;
- wherein the plurality of sensors are arranged on the rear side of the concrete-contacting layer, such that the plurality of sensors touches the rear side of the concrete-contacting layer, wherein an arrangement of the plurality of sensors is circular.

14. The formwork panel according to claim 13,
- wherein the plurality of sensors are configured to measure one or more of a temperature, a pressure, a humidity, a tensile force, an elongation, a bending, or a PH value.

15. The formwork panel according to claim 14,
- wherein the formwork panel comprises a panel core,
- wherein the plurality of sensors are disposed between the concrete-contacting layer and the panel core or within the panel core.

16. A formwork panel for a formwork device for producing wall or ceiling sections in fresh concrete construction, comprising:
- a concrete-contacting layer configured to come into direct contact with the concrete to be poured into the formwork device;
- a plurality of sensors integrated in the formwork panel;
- wherein the plurality of sensors are arranged on the rear side of the concrete-contacting layer, such that the plurality of sensors touches the rear side of the concrete-contacting layer, wherein an arrangement of the plurality of sensors is rectangular.

17. The formwork panel according to claim 16,
- wherein the plurality of sensors are configured to measure one or more of a temperature, a pressure, a humidity, a tensile force, an elongation, a bending, or a PH value.

18. The formwork panel according to claim 17,
- wherein the formwork panel comprises a panel core,
- wherein the plurality of sensors are disposed between the concrete-contacting layer and the panel core or within the panel core.

19. A formwork panel for a formwork device for producing wall or ceiling sections in fresh concrete construction, comprising:
- a concrete-contacting layer configured to come into direct contact with the concrete to be poured into the formwork device; and
- a plurality of sensors integrated in the formwork panel;

wherein the plurality of sensors are arranged on the rear side of the concrete-contacting layer, such that the plurality of sensors touches the rear side of the concrete-contacting layer, wherein an arrangement of the plurality of sensors is elliptical.

20. The formwork panel according to claim 19, wherein the plurality of sensors are configured to measure one or more of a temperature, a pressure, a humidity, a tensile force, an elongation, a bending, or a PH value.

21. The formwork panel according to claim 19 wherein the formwork panel comprises a panel core, wherein the plurality of sensors are disposed between the concrete-contacting layer and the panel core or within the panel core.

* * * * *